(12) United States Patent
Maurin

(10) Patent No.: US 7,167,626 B2
(45) Date of Patent: Jan. 23, 2007

(54) DEVICE FOR FIXING A RIGID AND BRITTLE FIBER COMPRISING A MECHANICALLY DEFORMABLE CLADDING AND LIABLE TO BE SUBJECTED TO AT LEAST ONE MECHANICAL STRESS

(75) Inventor: Laurent Maurin, Orsay (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 10/519,929

(22) PCT Filed: Jul. 4, 2003

(86) PCT No.: PCT/FR03/02079

§ 371 (c)(1),
(2), (4) Date: Dec. 30, 2004

(87) PCT Pub. No.: WO2004/007127

PCT Pub. Date: Jan. 22, 2004

(65) Prior Publication Data
US 2005/0232568 A1    Oct. 20, 2005

(30) Foreign Application Priority Data
Jul. 8, 2002    (FR) .................................. 02 08536
Jul. 18, 2002    (FR) .................................. 02 09117

(51) Int. Cl.
*G02B 6/00*    (2006.01)
(52) U.S. Cl. ...................................... 385/137; 385/136
(58) Field of Classification Search ................ 385/137, 385/136
See application file for complete search history.

(56) References Cited

U.S. PATENT DOCUMENTS

| 2,583,885 | A | | 1/1952 | Russenberger |
| 3,246,903 | A | | 4/1966 | Sattler |
| 4,848,870 | A | * | 7/1989 | Wisecarver et al. .......... 385/55 |
| 5,002,359 | A | * | 3/1991 | Sayegh ........................ 385/107 |
| 5,259,174 | A | | 11/1993 | Fargeas et al. |
| 5,495,425 | A | | 2/1996 | Kanaan |
| 5,530,785 | A | | 6/1996 | Sakamoto et al. |

FOREIGN PATENT DOCUMENTS

| DE | 36 03 616 A1 | 8/1987 |
| EP | 0 461 339 A2 | 12/1991 |

* cited by examiner

*Primary Examiner*—Brian Healy
*Assistant Examiner*—Jerry Martin Blevins
(74) *Attorney, Agent, or Firm*—Pearne & Gordon LLP

(57) ABSTRACT

The purpose of this invention is a device (1) for fixing a fiber (2) comprising a rigid and brittle core (24) surrounded by a mechanically deformable cladding (22), and that can be subjected to at least one mechanical stress. According to the invention, the clamping device comprises concentric jaws (4), each jaw comprising an inner surface (14) composed of a central portion (16) and two end portions (18, 20), the end portions being made so as to prolong the central portion by gradually moving away from the main axis of the device, each comprising at least one part in contact with the mechanically deformable cladding when the jaw occupies a clamped position.

Use of this device for fixing an optical fiber and any optical fiber sensor, particularly a Bragg grating optical fiber sensor.

10 Claims, 3 Drawing Sheets

DEVICE FOR FIXING A RIGID AND BRITTLE FIBER COMPRISING A MECHANICALLY DEFORMABLE CLADDING AND LIABLE TO BE SUBJECTED TO AT LEAST ONE MECHANICAL STRESS

TECHNICAL DOMAIN

This invention generally relates to a device for fixing a fiber composed of a core made of a rigid and brittle material surrounded by a less rigid and mechanically deformable cladding, the fiber possibly being subjected to at least one mechanical stress once fixed onto the device.

One preferred application of the invention relates to fixing optical fibers, these fibers particularly being made with an $S_iO_2$ core.

Examples of this type of clamping device include particularly an application in the field of strain gages comprising an optical fiber inside which at least one Bragg grating is photo-inscribed, and another application in the field of optical fiber sensors with Bragg gratings such as gas pressure or density sensors.

STATE OF PRIOR ART

In this technical domain related to fastening a fiber composed of a core made of a rigid and brittle material surrounded by a less rigid and mechanically deformable cladding, onto a particular support, known techniques apply particularly to fastening of an optical fiber. Several embodiments have already been proposed in prior art.

A first technological solution is known consisting of bonding the optical fiber onto a mechanical support.

However, this solution has several serious disadvantages, particularly that most of the mechanical strength is lost when the ambient temperature reaches about 200° C.

To overcome this problem of mechanical strength related to conventional glues, it has been proposed to use high performance glues such as glues containing for example silica, or ceramic glues. This type of glue can easily bond the optical fiber onto the mechanical support at relatively high temperatures.

On the other hand, when these high performance glues are used, the stiffness of the glues is so high that it introduces shear stresses at the boundary of the gluing area, significantly reducing possible means of manipulating the bonded assembly, since the bonded assembly is very brittle and can be damaged when it is moved.

Furthermore, polymerization of high performance glues and ceramic glues that are like cements, requires input energy that can damage the protective deformable cladding around the core of the optical fiber, typically composed of $S_iO_2$. Furthermore, when the input energy is made by inputting heat, use of the first proposed technological solution cannot be considered in media in which heat is unacceptable, for example due to the risks of explosion.

Furthermore, aging of the glue causes a serious modification of its rheological properties, which vary with time in a completely unknown manner. Thus, over a relatively long period, the change in properties such as Young's modulus makes it impossible to know the characteristics related to adhesion and shear of the glues.

Note that when the optical fiber is subjected to a tension stress, this fiber applies a shear force on the glue. Thus, this shear force is additional to the shear of the mechanically deformable cladding of the optical fiber, thus causing a serious measurement error when the optical fiber is used in a strain gage. In this respect, note that a strain gage is a typical example in which very high fiber bonding precision is necessary, firstly to achieve the metrological quality of the device containing the mandrel, and secondly to reduce the calibration dispersion between several of these devices.

Finally, note that due to lack of perfect control over the glue flow, the technology used is incapable of achieving easy reproducibility of the anchor. Furthermore, the assembly made between the optical fiber and the mechanical support cannot be disassembled without damaging the optical fiber, which is a serious disadvantage considering the relatively high cost of a Bragg grating optical fiber.

A second technological solution proposed in prior art relates to welding of the optical fiber onto a mechanical support, the fiber having firstly been metallized on the surface.

For example, welding may be also done by means of local melting of a drop of material identical to that from which the core of the optical fiber to be held in place is made.

However, in the case of an added metallic coating around the fiber, it is difficult to make the attachment bond to the extent that the welding points need to be made on small contact surfaces, and consequently have to be applied with extreme precision so as to not damage the optical fiber.

As in assemblies by gluing mentioned above, reproducibility of the weld is difficult to achieve so that the mechanical behavior of the assembly cannot be determined precisely. Furthermore, note that the mechanical behavior of the assembly is particularly difficult to determine since the weld itself causes a metallurgical transformation, modifying the mechanical characteristics of the assembly.

Furthermore, apart from the fact that this type of assembly cannot be made in media in which energy cannot be input, the forces that the connection between the optical fiber and the metallic coating can resist are relatively low. The resulting connection is not a real physical connection, and therefore cannot resist high forces. Furthermore, tests carried out have demonstrated that when high stresses are applied on the fiber, the metallic coating is separated and then slides on this optical fiber since the protective cladding is usually made of polymer (generally polyimide or polyacrylate).

Finally, as in the first technological solution mentioned above, the assembly obtained by welding is an irreversible assembly and in the worst case the optical fiber cannot be disassembled without breaking it, and even in the best case the mechanical characteristics of the optical fiber will be degraded.

Unlike the solutions mentioned above, a third technological solution proposed in prior art can give a removable assembly. It involves a capstan fixed in rotation, around which the fiber is wound in one or several turns.

However, this type of assembly is not satisfactory either since it cannot completely prevent the optical fiber from sliding when a tension stress is applied to it. This type of assembly is used particularly in the field of tensile testing machines for rheology, and may comprise rubber jaws arranged in parallel, so as to minimize sliding of the optical fiber. Nevertheless, despite the presence of these deformable jaws, tests have demonstrated that when such an optical fiber clamping device is used, sliding inevitably occurs as soon as the tension force exceeds a value of 5 N, which corresponds to an elongation of 0.5% of a 125 μm diameter standard optical fiber excluding protective claddings, which is the size widely used in the telecommunications field.

It was also noted that winding around the capstan causes optical losses essentially due to the appearance of macro-curvatures on the fiber, which are extremely harmful to good transmission of a signal through this optical fiber. Note that in order to obtain negligible optical losses, the radius of curvature of an optical fiber wound around a capstan must be considerably increased, for example up to a value of more than one centimeter for conventional single mode fibers. In this case, the size of the clamping device will then be too large for use in the composition of a Bragg grating optical fiber sensor.

OBJECT OF THE INVENTION

Therefore, the purpose of the invention is to propose a device for fixing a fiber comprising a rigid and brittle core surrounded by a mechanically deformable cladding such as an optical fiber, the fiber possibly being subjected to at least one mechanical stress, the device at least partially overcoming the disadvantages mentioned above related to embodiments according to prior art.

More precisely, the purpose of the invention is to present a clamping device enabling assembly and disassembly of the rigid and brittle fiber without damaging it and without applying macro-curvatures to it, and capable of holding the fiber in place without sliding when a mechanical stress such as a high tension stress is applied to it. This tension force may for example be as high as 50 N in the special case in which this fiber is an optical fiber of a standard type used in the telecommunications field.

Furthermore, another purpose of the invention is to propose a device for fixing a fiber that can resist ambient temperatures of more than 200° C., with a sufficiently small size to be used in the composition of an optical fiber strain gage, or a Bragg grating optical fiber sensor.

To achieve this, the object of the invention is a device for fixing a fiber comprising a rigid and brittle core surrounded by a mechanically deformable cladding, the device comprising several jaws distributed around a main axis of this device, each jaw comprising an inner surface composed of a central portion and two end portions, the end portions being made so as to prolong the central portion by gradually moving away from the main axis of the device, remaining at least partly in contact with the mechanically deformable cladding when the jaw occupies a clamped position. This progressive extension is preferably done by a surface with the same tangent as the central portion at the point at which it is connected.

Advantageously, the clamping device proposed by the invention is designed such that when they are in their maximum concentric clamping position, the jaws leave an orifice free along the axis of the mandrel, at least large enough to allow the rigid fiber core to pass through without being deformed by it. Thus, the mechanically deformable cladding absorbs the deformations that occur when the mandrel is clamped. This enables repeated assembly and disassembly of the fiber, without the need to break or weaken the fiber.

The same characteristic can also be defined in that when the jaws are clamped to the maximum in any plane perpendicular to the axis of the mandrel, they leave a hole free around this axis, the smallest diameter of the hole starting from this axis being equal to at least the outside radius of the rigid and brittle core of the fiber.

If the device according to the invention is used to hold an optical fiber, the deformation of the fiber caused by concentric clamping of the jaws is applied exclusively on the mechanically deformable cladding usually made of polymer, and not on the silica core of the fiber through which the optical transmission takes place. This is explained particularly by the fact that the cladding, preferably made of polyimide, has a Young's modulus about thirty times lower than the Young's modulus of silica, normally used to make up the core of the optical fiber. Furthermore, this factor may be significantly higher when the cladding is made of polyacrylate.

Thus, it is relatively easy to adapt the design of the device so as to obtain a very strong removable anchor, not causing any mechanical or optical degradation of the fiber core, and consequently not introducing any mechanical weakening or optical loss. For example, tests carried out have shown that for a jaw length of approximately 10 mm and a standard 125 μm diameter and 100 mm long optical fiber with a silica core, the clamping device according to the invention is capable of holding the optical device in place without breakage and without sliding, for tension forces of up to 50 N. For information, note that solutions proposed according to prior art cannot resist tension forces of the order of 5 N before causing sliding of the fiber or breakage of the fiber.

The technological solution was selected particularly due to the observation that a fiber with a rigid and brittle core such as an optical fiber, is capable of resisting very strong radial compression forces, and consequently can resist compression stresses generated by concentric clamping jaws. Nevertheless, in prior art, concentric clamping jaws were never used to make clamping devices for this type of fiber. This is particularly due to the existence of a technical preconception designed to use clamping jaws solely to hold non-brittle materials, in which the elastic area is directly connected to a ductile area, to prevent a clean break of the material as soon as a particular stress level is applied.

Furthermore, after carrying out other analyses that led to the conclusion that the breakage of an optical fiber held in place by clamping jaws was due to local shear stresses at the ends of the jaws rather than compression stresses that can easily be resisted by the silica fiber core, the clamping device according to the invention was designed to generate minimum shear in the fiber. The device was also designed particularly to limit shear in the optical fiber at the parts of the fiber at which a maximum stress concentration occurs, namely at parts in contact with the ends of each jaw. Thus, the invention was made by overcoming a technical preconception existing in the field considered, by providing a clamping device comprising jaws with an internal surface in which the ends of the surface progressively move further away from the main axis of the device so as to reduce the stress gradient developed by the clamping force, thus attenuating the intensity of the shear to be resisted by the fiber being held.

Consequently, when the fiber is an optical fiber equipped with at least one Bragg grating in order to make strain gage measurements, the reduction in the shear forces resulting from direct contact of the jaws with the cladding, also considerably reduces the measurement error, particularly compared with techniques consisting of inputting an additional deformable material medium such as glue between the fiber and the attachment support. For example, for a tension force of 10 N, it has been observed that the induced error on the measurement of the deformation using the Bragg grating was of the order of $10^{-7}$, in other words less than the intrinsic resolution of a standard Bragg grating.

Furthermore, the very simple design of the device according to the invention makes it possible to further reduce deformation of the fiber, for example by increasing the jaw length in order to distribute the clamping force over a greater contact surface area, in order to reduce radial clamping stresses in the same proportions. Note that this increase in the length of the jaws can also contribute to reducing the measurement error due to assembly to a value less than the intrinsic resolution of a standard Bragg grating.

Furthermore, the proposed clamping device enables an exclusively mechanical bond of the optical fiber, enabling its use in media in which energy cannot be added by heating.

Finally, note that constituent elements of the clamping device according to the invention, which is applicable to any fiber type element comprising a rigid and brittle core surrounded by a mechanically deformable cladding, can easily be made sufficiently small so that they can be applied to optical fibers and integrated in any optical fiber sensor, particularly a Bragg grating optical fiber sensor, in which the principle consists of measuring a physical magnitude by the variation of the fiber length.

Preferably, for each jaw, the end portions are surfaces for which a section defined by any plane passing through the main axis of the device is a straight segment or a curved line. Advantageously, the junctions between the central portion and the end portions may be polished such that the inner surface does not have a sharp angle, this specific characteristic further reducing the shear stress applied on the optical fiber.

Preferably, the inner surface of each jaw is a surface with no sharp angle, in other words, for each jaw, the end portions and the central portion of each inner surface are surfaces that join together tangentially, such that their intersection with any plane passing through the main axis of the device is a continuous curved line with no sharp point.

Preferably for each jaw, the inner surface is a surface for which the section defined by any plane perpendicular to the main axis of the device is an arc of circle with a radius greater than the nominal outside radius of the mechanically deformable cladding. Thus, when the jaws of the device are clamped onto the optical fiber, the shape of the inner surface of each of the jaws is particularly well adapted to generate progressive and uniform deformation of the cladding.

Another possible solution would be to arrange for the inner surface of each jaw to be a surface for which a section defined by any plane perpendicular to the main axis of the device is a line segment, such that at least the central portion of the inner surface is a plane surface that can easily be made by machining.

Preferably, when the jaws are in their clamped position, a section through the inner surfaces defined by any plane perpendicular to the main axis of the device is a closed line. This advantageously enables quasi-uniform deformation of the cladding, to prevent accidental crushing of the rigid and brittle core of the fiber, the shear stress in this cladding being even lower when only part of the end portions of each jaw are in contact with this mechanically deformable cladding.

Preferably, the jaws of the device are stainless steel jaws resisting ambient temperatures of up to at least 200° C. Since all elements are metallic and non-oxidizable, none of them are likely to degrade under the effect of heat, and the strain gage measurement error caused by expansion of the jaws has been evaluated as being less than the intrinsic resolution of a standard Bragg grating photo-inscribed in a silica fiber coated with a polyimide cladding with a standard thickness of about 10 μm, when the length of the jaws do not exceed 10 mm.

Finally, it would also be possible for each jaw to have an outer surface in the shape of a portion of a cone, each outer surface being capable of cooperating with a complementary conical inner surface provided on a jaw support of the device. For example, by designing a complementary conical surface with a cone angle measured in a plane intersecting its axis of symmetry equal to about 7°, simple hand tightening is sufficient to enable the clamping device to resist tension forces of approximately 20 N. Furthermore, as mentioned above, higher performance clamping using an appropriate tool can enable tension forces of the order of 50 N without causing any degradation to the optical fiber core, provided that the jaw geometry is such that when they are clamped to the maximum, there is an opening between them with a diameter equal to at least the fiber core diameter.

Other advantages and characteristics of the invention will become clearer after reading the non-limitative detailed description given below.

BRIEF DESCRIPTION OF THE FIGURES

This description will be made with reference to the appended figures wherein.

DETAILED DESCRIPTION OF PREFERRED EMBODIMENTS

Figure 1:
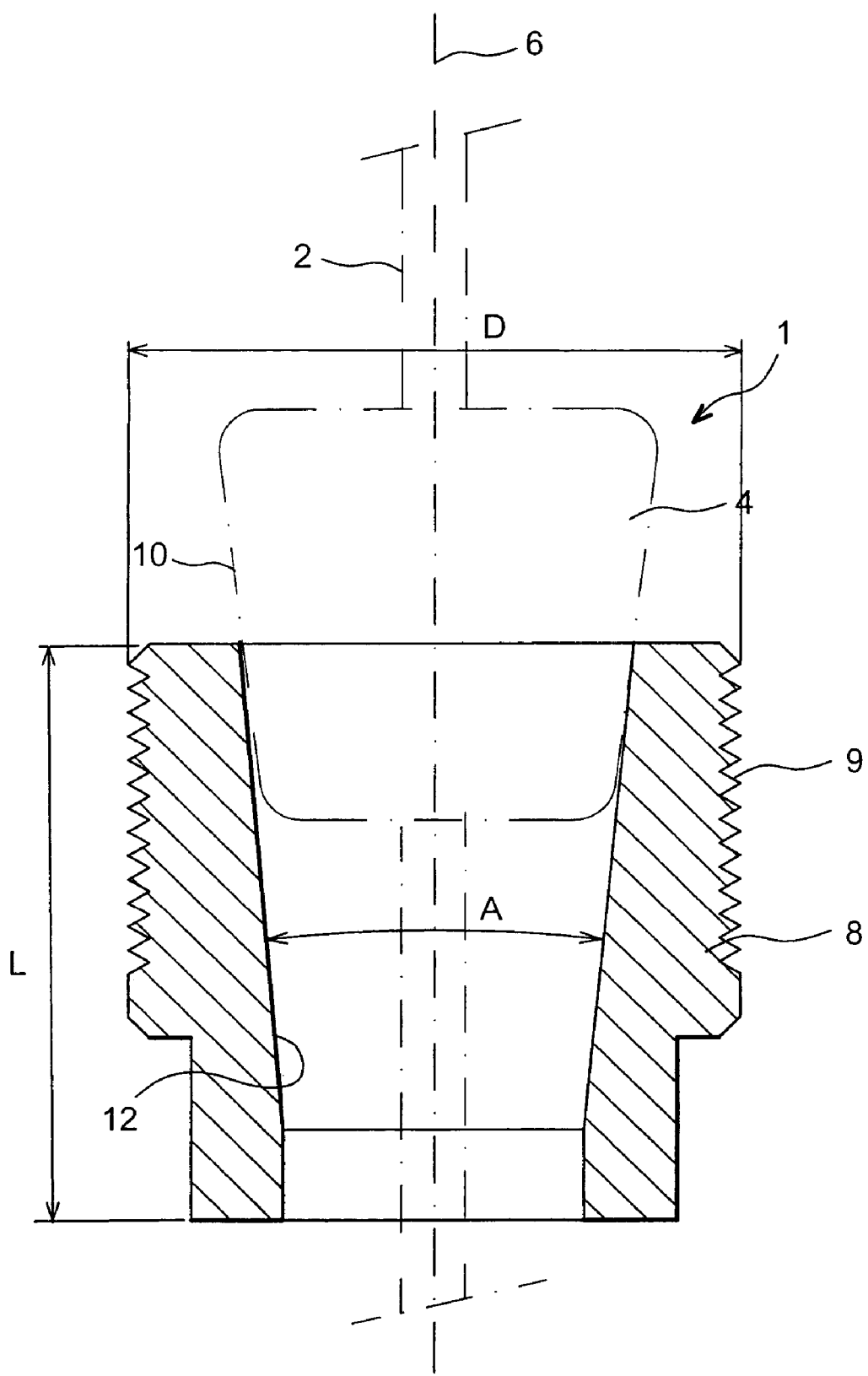
FIG. 1 shows a sectional view of the clamping device according a preferred embodiment of this invention.

FIG. 1 shows a device 1 for fixing an optical fiber 2, according to a preferred embodiment of this invention. The term "optical fiber" will be used throughout the remainder of the description, but it is obviously possible to apply this invention to any fiber type element comprising a rigid and brittle core surrounded by a mechanically deformable cladding.

This type of device 1 can be used in different systems, and more specifically in systems in which the optical fiber 2 is subjected to at least one mechanical stress such as tension.

Thus for guidance, the clamping device 1 can be used in the composition of a strain gage with at least one Bragg grating, for example for monitoring of bridges, or for the composition of a Bragg grating optical fiber sensor, of the gas pressure or density type sensor. Furthermore, the device 1 can also be used in mechanical rheology testing machines, to maintain the optical fiber for which technical characteristics such as the tensile strength need to be determined. Thus, in most systems in which the clamping device 1 is used, two of these devices are usually necessary so that each of the two ends of the optical fiber 2 can be clamped.

The clamping device 1 comprises several jaws 4 distributed around a main axis 6 of the device 1, which is coincident with the longitudinal axis of the fiber 2 when the fiber is held on device 1. The jaws 4 are placed in a jaw support 8, this support possibly being assembled on an arbitrary mechanical support (not shown) for example by screwing using its threaded outer surface 9. The clamping jaws 4 preferably each have an outer surface 10 in the form of a conical portion, cooperating with a complementary conical inner surface 12 provided on the jaw support 8.

Thus, activation of a clamping system (not shown) of the device 1 means that the jaws 4 can be slid towards the top of the complementary conical inner surface 12, and consequently can generate radial clamping of the optical fiber 2 located between the jaws 4. Preferably, the clamped optical fiber 2 comprises at least one Bragg grating (not shown), away from the part in contact with the device 1. Note that the clamping device 1 may be designed to be self-clamping, namely so that the assembly formed by the device 1 and the optical fiber 2 can be held in radial compression simply by pulling on the optical fiber, taking account of the non-zero friction between the jaws 4 and the outer surface of the cladding of the optical fiber 2. Furthermore, the optical fiber 2 can be fastened on the clamping device 1 at any point on this fiber, since it is held on device 1 exclusively through simple mechanical clamping.

Note that for a cone angle A equal to about 7°, a length L of the jaw support 8 equal to about 14 mm and an outside diameter D of the order of 10 mm, manual activation of the clamping system of the device 1 can maintain an optical fiber for which the outside diameter of the cladding is 150 µm, without sliding or rupture, for tension forces of up to 20 N. Furthermore, activation of the clamping system using an appropriate tool can increase the value of the maximum tension force up to 50 N.

Figure 2:
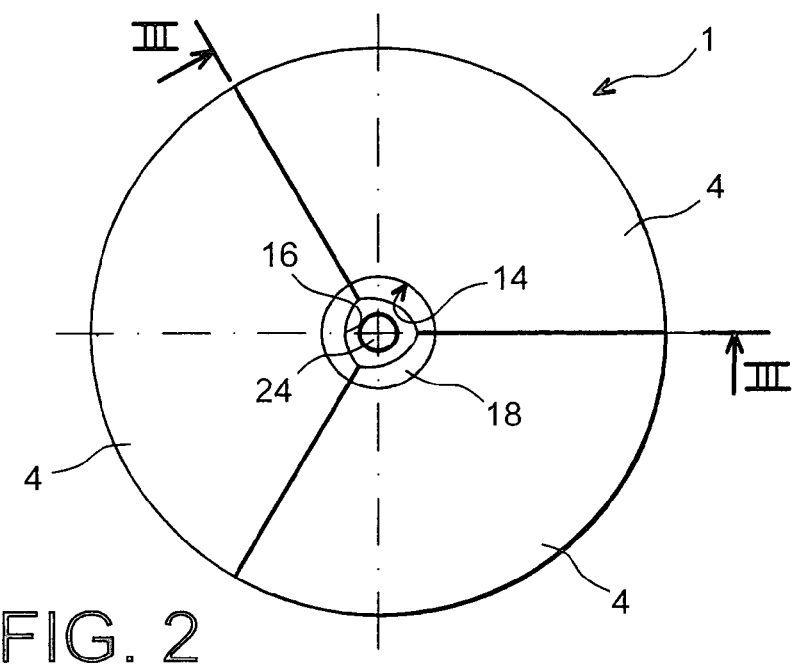
FIG. 2 shows a partial top view of the clamping device shown in FIG. 1, when the jaws of the device are in a clamping position.
Figure 3:
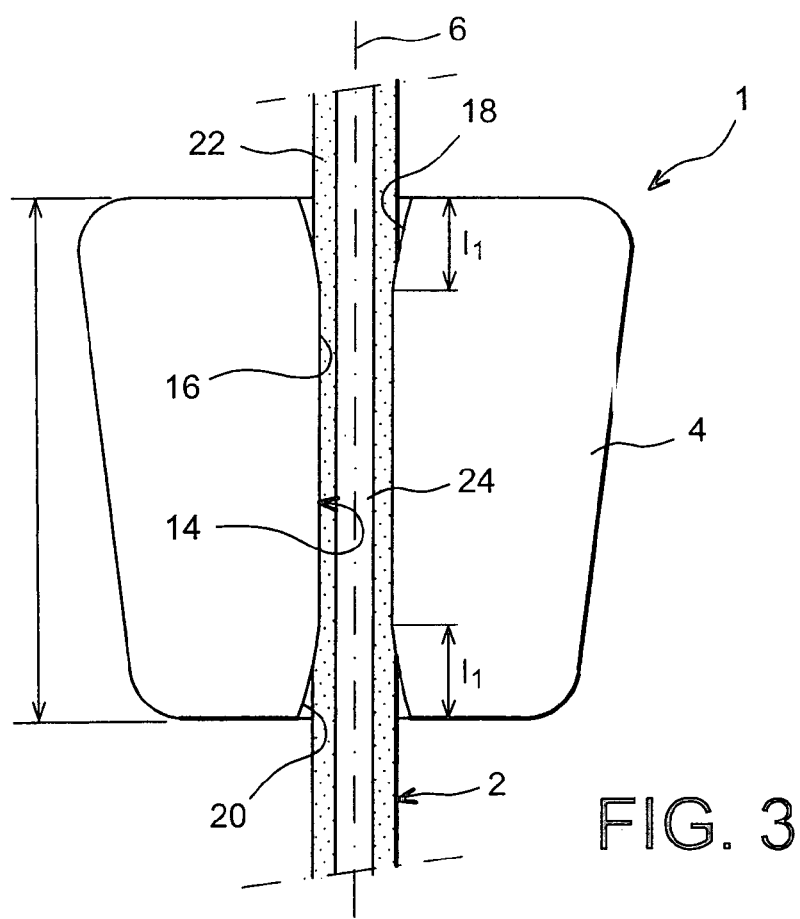
FIG. 3 shows a sectional view taken along line III—III in FIG. 2, showing cooperation between the jaws and the optical fiber held in place between the jaws.

FIGS. 2 and 3 more precisely illustrate the clamping jaws 4 used in the clamping device 1 in FIG. 1, when they are in a clamping position and cooperate with an optical fiber 2. Note that for reasons of clarity, only the core 24 of the optical fiber 2 cooperating with the clamping jaws 4 has been shown in FIG. 2.

There are three clamping jaws 4 in the preferred embodiment of the clamping device 1 described herein. Naturally, there could be more then three jaws 4 without departing from the scope of the invention.

In order to hold the optical fiber 2 in place with respect to the device 1, the clamping jaws 4 each have an inner surface 14 consisting of a central portion 16 prolonged by two end portions 18 and 20, located on each side of the central portion 16.

As can be clearly seen in FIG. 2, the jaws 4 in the clamping position are in contact with each other, so as to apply a relatively uniform pressure on the optical fiber 2 held in compression. In other words, a section of the inner surfaces 14 on any plane perpendicular to the main axis 6 of the device 1 is a closed line when the jaws 4 are clamped to the maximum.

Therefore the jaws 4 used preferably have a length l of the order of 12 mm, and hold the optical fiber 2 in place by clamping. The clamping device 1 is then designed such that clamping of the optical fiber 2 only deforms the mechanically deformable outer cladding 22, provided to protect the core 24 of this fiber. Thus, neither the optical transmission characteristics of the fiber 2 nor its mechanical characteristics are deteriorated by clamping, which can be achieved by means of the mechanically deformable polymer cladding 22, while the core 24 of this fiber is normally made of silica. Note that the optimal clamping pressure of the optical fiber 2 causing deformation of the cladding 22 without causing deformation of the core 24, has been measured to be about $10^8$ Pa for a polyimide cladding 22 with a nominal thickness of approximately 10 µm, corresponding to its average thickness before it is compressed.

The clamping jaws 4 are preferably made from a sufficiently rigid material so as not to be deformed at the contact of the cladding 22 of the fiber 2 when they are in the clamping position. For example, the clamping jaws 4 will preferably be metallic to cause deformation of the mechanically deformable cladding 22 without being deformed themselves.

As can be seen in FIG. 3, the end portions 18 and 20 of each jaw 4 of the clamping device 1 prolong the central portion 16 of the inner surface 14, gradually moving further away from the axis 6 of the device 1. The purpose of this specific characteristic is to reduce the shear of the mechanically deformable cladding 22, at the location at which the shear stress generated is theoretically the highest, namely at the ends of the jaws 4. In this way, the mechanically deformable cladding 22 is deformed and compressed progressively along at least part of each of the end portions 18 and 20, and consequently enables the optical fiber 2 to resist high tension forces without being broken or mechanically damaged.

Note that the "smoothed" geometry of the inner surfaces 14 of the jaws 4 also enable the optical fiber 2 to be loaded in tension along an axis moving away from the main axis 6 of the device 1 by an angle of a few degrees, without causing breakage of this fiber when it is manipulated.

Preferably, the jaws 4 are designed such that when they are in their clamping position, only part of each end portion 18 and 20 is in contact with the mechanically deformable cladding 22 of the optical fiber 2. For example, it would be possible for part of each of the end portions 18 and 20 in contact with the fiber 2 to be equivalent in terms of surface area to ⅓ of the total surface area of the end portion 18, 20 concerned. Thus, at the junction between any one of the end portions 18, 20 and the central portion 16 of the inner surface 14, the mechanically deformable cladding 22 is compressed to a maximum without causing excessive deformation for the material from which the cladding 22 is made, and very much below the stress threshold that would damage the core 24 of the fiber 2, while the compression force gradually reduces until the mechanically deformable cladding 22 is no longer in contact with the end portion 18, 20 and returns to its nominal outside diameter.

In this preferred embodiment of the clamping device 1 according to the invention, the end portions 18 and 20 for each jaw 4 are surfaces for which a section in any plane passing through the main axis 6 of the device 1 is a curved line. This solution very much facilitates progressive deformation of the mechanically deformable cladding 22, and the reduction in the shear force applied to this optical fiber 2.

Preferably, the curved line could follow an arc of a circle extending over a length $l_1$, along the main axis 6 of the device 1, the length $l_1$ corresponding to about ⅙ of the total length l of the jaw 4 along the same axis.

Still with reference to FIGS. 2 and 3, for each jaw 4 of the clamping device 1, the inner surface 14 is a surface for which a section defined by any plane perpendicular to the main axis of the device is an arc of circle with a radius greater than the outside radius of the mechanically deformable cladding 22. Note that the radius of this arc of circle is constant over the entire central portion 16. But if this plane perpendicular to the axis moves further from the central portion 16 and intersects one of the end portions 18 or 20, the radius of this arc of circle increases. For example, as can be seen in FIG. 2, the closed line corresponding to the section of the inner surfaces 14 at the central portions 16 is composed of three identical arcs of circle, the end of one arc joining the next arc.

Note also that the inner surfaces 14 are designed such that when the jaws 4 are in the clamping position, the central portions 16 define a laterally closed space designed to be sufficiently large to hold an optical fiber 2 with no mechanically deformable cladding. In other words, when the jaws 4 are clamped to the maximum as shown in FIG. 2, in any plane perpendicular to the main axis 6, these jaws 4 form a closed line centered on the axis 6, and for which the shortest distance between the axis 6 and the closed line is at least equal to the outside radius of the rigid and brittle core 24 of the fiber 2. With such a design, the core 24 of the optical fiber 2 is not deformed during clamping of the jaws 4, unlike the mechanically deformable polymer cladding 22 that has a Young's modulus about thirty times less than the Young's modulus of the silica core 24, in the case of a standard fiber with a polyimide cladding.

Finally, to further avoid the unwanted effect of shear forces on the optical fiber 2, the junctions between the central portion 16 and the end portions 18 and 20 may be polished, in order to minimize the concentration of shear stresses at these junctions. It is then possible to polish to the nearest micron, using means frequently used when the surfaces to be polished will come into contact with an optical fiber.

Figure 4:
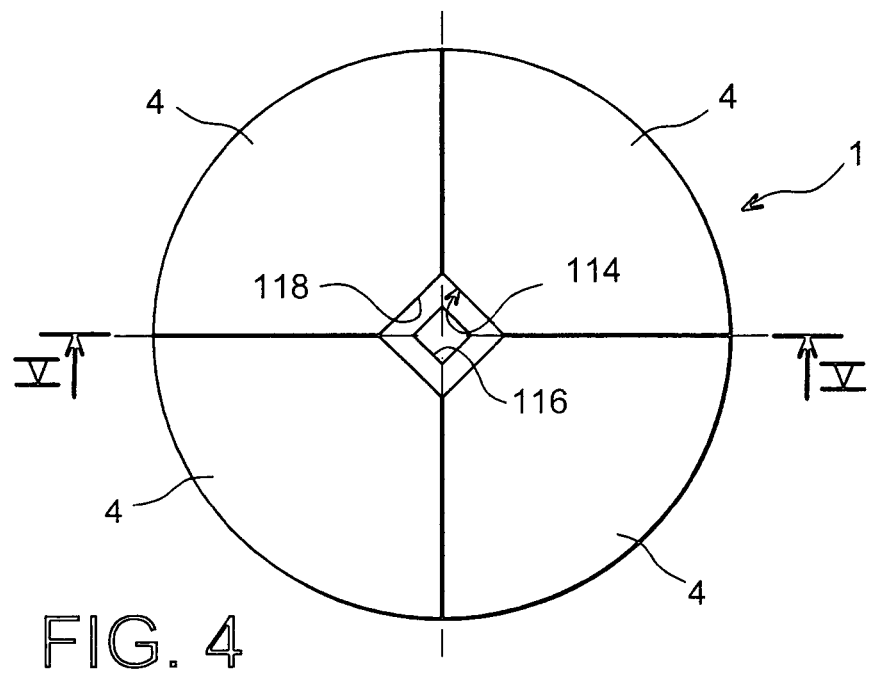
FIG. 4 shows a partial top view of the clamping device according to another preferred embodiment of this invention, when the jaws of the device are in a clamped position.
Figure 5:
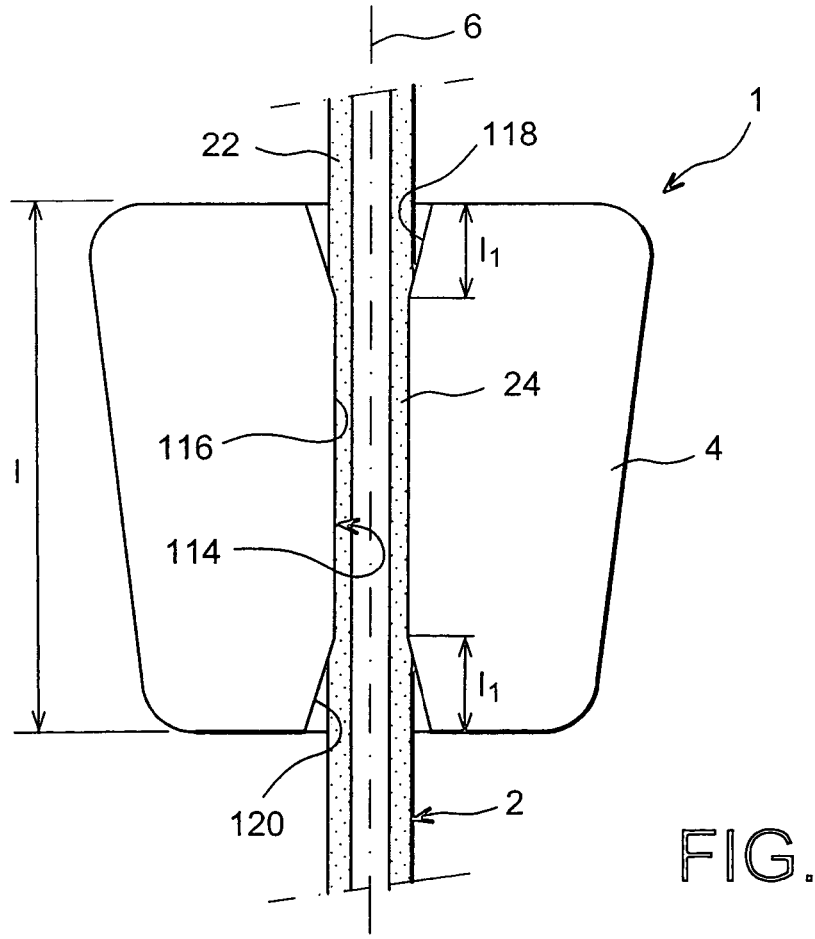
FIG. 5 shows a sectional view taken along line V—V in FIG. 4, showing cooperation between the jaws and the optical fiber held in place between the jaws.

According to another preferred embodiment of this invention shown in FIGS. 4 and 5, only the geometry of the inner surface 114 of the jaws 4 and the number of these jaws 4 are different from the preferred embodiment described above.

The clamping jaws 4 are identical, and there are four of them, always in contact with each other when they are in the position clamping the optical fiber 2. Obviously, there could be more than four jaws 4 without departing from the scope of the invention.

As above, for each clamping jaw 4 of the device 1, the inner surface 114 comprises a central portion 116 prolonged by two end portions 118 and 120 moving progressively away from the main axis 6 of the device 1. Furthermore, each portion 116, 118 and 120 of the inner surface 114 has dimensions similar to the dimensions of the portions 16, 18 and 20 in the previous embodiment.

More specifically, with reference to FIG. 5 in which cooperation between the jaws 4 and the optical fiber 2 is shown (the optical fiber not being shown in FIG. 4 for reasons of clarity), the end portions 118 and 120 are surfaces for which a section defined by any plane passing through the main axis 6 of the device 1 is a line segment. Furthermore, the inner surface 114 is a surface for which a section according to any plane perpendicular to the main axis 6 of the device 1 is a line segment.

In other words, it will be possible for the central portion 116 of the inner surface 114 to be a plane surface, and the end portions 118 and 120 are also chamfer type plane surfaces. In any case, when the jaws 4 are in their clamping position, a section of the inner surfaces 114 defined by any plane perpendicular to the main axis 6 of the device 1 is a closed line, of the type forming a square. When the section of inner surfaces 114 is taken at any level of the central portions 116, the square section is always identical and the length of the side of this square is greater than the diameter of the core 24 of the optical fiber 2. On the other hand, due to the presence of chamfer type surfaces, the square section at the end portions 118 and 120 increases as the distance from the central portions 116 increases.

When making clamping jaws 4 of this type, which is particularly easy by machining or polishing due to the planeness of the surfaces, the junctions between the central portion 116 and the end portions 118 and 120 should be carefully polished, for example to the nearest micron. As a result, as in the previously described embodiment, the inner surface 114 does not have a sharp angle thus reducing the concentration of shear forces on the held optical fiber 2. In other words, the end portions 118 and 120 and the central portion 116 of each inner surface 114 are tangentially continuous with each other, such that their intersection with any plane passing through the main axis 6 of the device 1 is a line with no sharp point.

Since the plane geometry of the central portions 116 is not as well adapted to uniformly compressing the cladding 22 as the curved geometry of the previous embodiment, the central portions 116 need to have an excellent surface condition to avoid local overpressures. Overpressures can then be avoided by providing machining tolerances of the order of +0 and −0.005 mm for making the central portions 116.

Thus, as described above, the polymer mechanically deformable cladding 22 of the optical fiber 2 is progressively deformed along the end portions 118 and 120, until contact with these portions is lost and until its nominal outside diameter is restored. Furthermore, the ratio between the surface area of the parts of the end portions 118 and 120 in contact with the cladding 22 and the total surface area of these surfaces is similar to the ratio mentioned in the preferred embodiment described above.

Tests have shown that for a length l of the jaws 4 equal to the order of 12 mm, the clamping device 1 is capable of holding an optical fiber 2 without sliding or breakage, for a tension force close to 50 N. These tests were carried out using an optical fiber 2 with a nominal outside diameter equal to 150 µm measured on the outside of a standard polyimide cladding 22, but the clamping device 1 according to the invention may obviously hold larger diameters of optical or other fibers.

Moreover, the clamping device 1 presented in the two preferred embodiments mentioned above is particularly well adapted to high temperatures of about 200° C., provided that the elements of the device 1 are metallic and preferably non-oxidizable. Consequently, for clamping jaws 4 with a length l equal to approximately 10 mm, the expansion of these jaws is extremely small and does not have any influence on the strain gage measurements made. However, if the clamping jaws are longer, for example about 100 mm, the expansion phenomenon of the jaws becomes more significant and preferably should be neutralized so that measurements made between these jaws 4 are not distorted. The clamping jaws 4 can be made from metallic materials with low expansion, or a compensating mechanical assembly can be added to overcome this problem.

It is also naturally useful if the geometry of the inner surfaces 14 and 114 is not limited to the geometries described in the two preferred embodiments described above. For example, the geometry of the inner surfaces could be the result of a combination of the two geometries presented so as to have a curved central portion and plane end portions, or vice versa.

Obviously, those skilled in the art could make various modifications to the devices 1 for fixing an optical fiber 2 that has just been described, solely as non-limitative examples.

Finally, as mentioned above, this clamping device 1 can be used in the composition of any type of sensor in which a magnitude is measured by the variation of the length of a wire, a tube or a brittle fiber comprising a mechanically deformable cladding, and particularly an optical fiber. Among these optical fiber sensors, it is particularly suitable for Bragg grating sensors that detect very small variations in the length between two attachment points of a fiber carrying one or several of these gratings.

The invention claimed is:

1. Assembly comprising a clamping device (1) and a fiber (2) held by said device (1) and comprising a rigid and brittle core (24) surrounded by a mechanically deformable cladding (22), said clamping device being adapted to resist a tension force having a value exceeding 5 N exerted along a longitudinal axis of said fiber (2), said clamping device (1) comprising several jaws (4) distributed around a main axis (6) of this device (1) and occupying a clamped position, each jaw (4) comprising an inner surface (14, 114) composed of a central portion (16, 116) and two end portions (18, 20, 118, 120), said end portions (18, 20, 118, 120) being made so as to prolong the central portion (16, 116) by gradually moving away from the main axis (6) of said device (1), wherein a section of the inner surfaces (14, 114) on any plane perpendicular to the main axis (6) of the device (1) is a closed line, and wherein only part of each end portion (18, 20, 118, 120) is in contact with the mechanically deformable cladding (22) of the fiber (2).

2. Assembly according to claim 1, wherein for each jaw (4), the end portions (118, 120) are surfaces for which a section defined by any plane passing through the main axis (6) of the device (1) is a line segment.

3. Assembly according to claim 1, wherein for each jaw (4), the end portions (18, 20) are surfaces for which a section defined by any plane passing through the main axis (6) of the device (1) is a curved line.

4. Assembly according to claim 1, wherein the inner surface (14, 114) of each jaw (4) is a surface with no sharp angle.

5. Assembly according to claim 1, wherein for each jaw (4), the inner surface (14) is a surface for which a section defined by any plane perpendicular to the main axis (6) of the device (1) is an arc of circle with a radius greater than a nominal outside radius of the mechanically deformable cladding (22).

6. Assembly according to claim 1, wherein the inner surface (114) of each jaw (4) is a surface for which a section defined by any plane perpendicular to the main axis (6) of the device (1) is a line segment.

7. Assembly according to claim 1, wherein the jaws (4) of said device (1) are metallic jaws.

8. Assembly according to claim 1, wherein each jaw (4) also comprises an outer surface (10) in the form of a conical portion, each outer surface (8) cooperating with a complementary conical inner surface (12) provided on a jaw support (8) of said device (1).

9. Assembly according to claim 1, wherein the fiber is an optical fiber.

10. Assembly according to claim 1, wherein the assembly is adapted for use in a strain gage and/or in a Bragg grating optical fiber sensor.

* * * * *